US00PP13588P2

(12) United States Plant Patent
Dümmen

(10) Patent No.: US PP13,588 P2
(45) Date of Patent: Feb. 18, 2003

(54) NEW GUINEA IMPATIENS PLANT NAMED 'DUEPETBLUST'

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 09/996,365

(22) Filed: Nov. 30, 2001

(51) Int. Cl.[7] ..... A01H 5/00

(52) U.S. Cl. ..... Plt./318

(58) Field of Search ..... Plt./318

(56) References Cited

PUBLICATIONS

UPOV–ROM GTITM Computer Database 2002/03, GTI Jouve Retrieval Software, Citation for Impatiens 'Duepetblust'.*

* cited by examiner

*Primary Examiner*—Bruce R. Campell
*Assistant Examiner*—June Hwu
(74) *Attorney, Agent, or Firm*—C. A. Whealy

(57) ABSTRACT

A new and distinct cultivar of New Guinea Impatiens plant named 'Duepetblust', characterized by its upright, rounded and uniform plant habit; freely branching and freely flowering habit; purple and red bi-colored flowers that are positioned above and beyond the leaves; and dark green-colored leaves.

1 Drawing Sheet

BOTANICAL CLASSIFICATION/CULTIVAR DENOMINATION

*Impatiens hawkeri* cultivar Duepetblust.

BACKGROUND OF THE INVENTION

The present Invention relates to a new and distinct cultivar of New Guinea Impatiens plant, botanically known as *Impatiens hawkeri*, and hereinafter referred to by the name 'Duepetblust'.

The new Impatiens is a product of a planned breeding program conducted by the Inventor in Rheinberg, Germany. The objective of the breeding program is to develop New Guinea Impatiens cultivars that have a uniform plant habit and attractive flower colors.

The new Impatiens originated from a cross made by the Inventor of a proprietary selection of *Impatiens hawkeri* identified as code number 94-120-1, not patented, as the female, or seed parent, with a proprietary selection of *Impatiens hawkeri* identified as code number 94-208-1, not patented, as the male, or pollen parent. The cultivar Duepetblust was discovered and selected by the Inventor as a flowering plant within the progeny of the stated cross in a controlled environment in Rheinberg, Germany.

Asexual reproduction of the new cultivar by terminal cuttings taken in Rheinberg, Germany, has shown that the unique features of this new Impatiens are stable and reproduced true to type in successive generations.

SUMMARY OF THE INVENTION

The following traits have been repeatedly observed and are determined to be the unique characteristics of 'Duepetblust'. These characteristics in combination distinguish 'Duepetblust' as a new and distinct Impatiens cultivar:

1. Upright, rounded and uniform plant habit.

2. Freely branching and freely flowering habit.

3. Purple and red bi-colored flowers that are positioned above and beyond the leaves.

4. Dark green-colored leaves.

Plants of the new Impatiens can be compared to plants of the female parent, the selection 94-120-1. In side-by-side comparisons conducted in Rheinberg, Germany, plants of the new Impatiens differed from plants of the selection 94-120-1 in the following characteristics:

1. Plants of the new Impatiens were stronger than plants of the selection 94-120-1.

2. Plants of the new Impatiens had darker green leaves than plants of the selection 94-120-1.

3. Flowers of plants of the new Impatiens were bi-colored whereas flowers of plants of the selection 94-120-1 were not bi-colored.

Plants of the new Impatiens can be compared to plants of the male parent, the selection 94-208-1. In side-by-side comparisons conducted in Rheinberg, Gernamy, plants of the new Impatiens differed from plants of the selection 94-208-1 in the following characteristics:

1. Plants of the new Impatiens were more compact than plants of the selection 94-208-1.

2. Plants of the new Impatiens had darker green leaves than plants of the selection 94-208-1.

3. Flowers of plants of the new Impatiens were bi-colored whereas flowers of plants of the selection 94-208-1 were not bi-colored.

Plants of the new Impatiens are similar to plants of the cultivar Guadeloupe, disclosed in U.S. Plant Pat. No. 10,001, in flower color. However, in side-by-side comparisons conducted in Rheinberg, Germany, plants of the new Impatiens differed from plants of the cultivar Guadeloupe in the following characteristics:

1. Plants of the new Impatiens were slightly taller and had longer internodes than plants of the cultivar Guadeloupe.

2. Plants of the new Impatiens were more freely branching than plants of the cultivar Guadeloupe.

3. Plants of the new Impatiens had larger flowers than plants of the cultivar Guadeloupe.

4. Plants of the new Impatiens were more freely flowering than plants of the cultivar Guadeloupe.

5. Flower color of plants of the new Impatiens was more intense than flower color of plants of the cultivar Guadeloupe.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Duepetblust' grown in a container.

DETAILED BOTANICAL DESCRIPTION

The cultivar Duepetblust has not been observed under all possible environmental conditions. The phenotype may vary somewhat with variations in environment such as temperature and light intensity without, however, any variance in genotype.

The aforementioned photographs, following observations and measurements describe plants grown in Rheinberg, Germany, under commercial practice in a glass-covered greenhouse, Plants were about 16 weeks from cuttings and were grown in 12-cm containers. During the production of the plants, day and night temperatures averaged 18° C. and light levels were about 4,500 lux.

In the following description, color references are made to The Royal Horticultural Society Colour Chart, edition 1995, except where general terms of ordinary dictionary significance are used.

Botanical classification: *Impatiens hawkeri* cultivar Duepetblust.

Parentage:

*Female parent.*—Proprietary selection of *Impatiens hawkeri* identified as code number 94-120-1, not patented.

*Male parent.*—Proprietary selection of *Impatiens hawkeri* identified as code number 94-208-1, not patented.

Propagation:

*Type cutting.*—Terminal cuttings.

*Time to initiate roots.*—Summer: About 7 days at 22° C. Winter: About 10 days at 22° C.

*Time to produce a rooted cutting.*—Summer: About 18 days at 22° C. Winter: About 25 days at 22° C.

*Root description.*—Fine and freely branching.

Plant description:

*General appearance.*—Upright, rounded and uniform plant growth habit; freely branching and flowering habit.

*Crop time.*—From unrooted cuttings, about 16 weeks are required to produce finished flowering plants in 12-cm containers.

*Plant height.*—About 20 cm.

*Plant diameter or spread.*—About 42 cm.

*Lateral branches.*—Quantity per plant: About ten. Length: About 17 cm. Diameter: About 8 mm. Internode length: About 6.2 cm. Color: 146B.

*Foliage description.*—Arrangement: Opposite or in whorls. Length: About 10.7 cm. Width: About 4.1 cm. Shape: Elliptic to ovate. Apex: Acuminate to apiculate. Base: Obtuse. Margin: Serrulate with ciliation. Texture: Smooth, glabrous; leathery. Venation pattern: Pinnate. Color: Young and fully expanded foliage, upper surface: 136A. Young and fully expanded foliage, lower surface: 59A. Venation, upper and lower surfaces: 59A. Petiole: Length: About 2.2 cm. Diameter: About 3 mm. Color, upper and lower surfaces: 59A.

Flower description:

*Flower type and flowering habit.*—Single rounded purple and red bi-colored flowers. Freely and continuously flowering; usually about five to seven flowers and flower buds per lateral branch. Flowers positioned above and beyond the foliage and typically face upward or outward. Petals self-cleaning; gynoecium persistent. Flowers not fragrant.

*Flower longevity.*—Flowers last about one week on the plant.

*Flowering season.*—Year-round under greenhouse conditions; in the garden, flowering from spring until fall. Plants begin flowering about six to seven weeks after planting.

*Flower buds.*—Length: About 1.2 cm. Diameter: About 8 mm. Shape: Ovoid. Color: 59A.

*Flower diameter.*—About 6 cm.

*Flower depth.*—About 2 cm.

*Petals.*—Quantity: Five per flower, imbricate. Length: About 3.1 cm. Width: About 3.8 cm. Shape: Obcordate. Apex: Notched, lobed. Base: Acute. Margin: Entire. Aspect: Mostly flat. Texture: Smooth; satiny. Color: When opening and fully opened, upper surface: Ground color, 74C; central longitudinal stripe, 45B; ground color fading to 74D with subsequent development. When opening and fully opened, lower surface: Ground color, 74C; central longitudinal stripe, 45A.

*Spur.*—Quantity: One per flower. Length: About 4.8 cm. Diameter: At apex: Less than 1 mm. At flower: About 2.5 mm. Aspect: Curved downward. Color: 149B.

*Peduncles.*—Length: About 4.9 cm. Diameter: About 1.5 mm. Strength: Moderately strong, flexible. Color: 145A.

*Reproductive organs.*—Androecium: Stamen quantity/arrangement: Five fused at anthers, hooded; filaments free. Anther length: About 5 mm. Anther shape: Oval. Anther color: Towards base, 155B, towards apex, 61C. Pollen amount: Abundant. Pollen color: 11D. Gynoecium: Pistil quantity: One per flower. Pistil length: About 6 mm. Stigma color: 74C. Style length: Less than 1 mm. Style color: 59B. Ovary arrangement: Five-celled. Ovary color: 59A.

*Seeds/fruits.*—Seed and fruit development has not been observed.

Disease/pest resistance: Plants of the new Impatiens have not been observed to be resistant to pathogens and pests common to Impatiens.

It is claimed:

1. A new and distinct cultivar of New guinea Impatiens plant named 'Duepetblust', as illustrated and described.

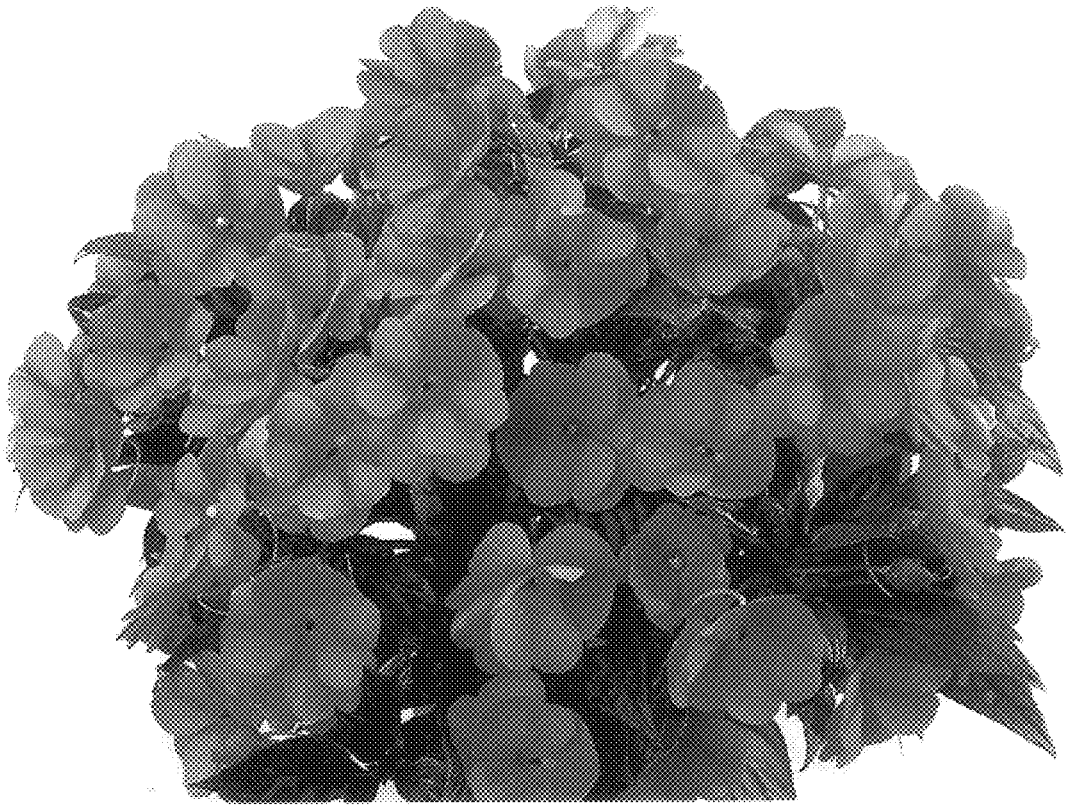

* * * * *